US012185654B2

(12) United States Patent
Allgaier

(10) Patent No.: US 12,185,654 B2
(45) Date of Patent: Jan. 7, 2025

(54) SPEED CONTROL OF IMPLEMENTS DURING TRANSITIONS OF SETTINGS OF AGRICULTURAL PARAMETERS

(71) Applicant: Precision Planting LLC, Tremont, IL (US)

(72) Inventor: Ryan Allgaier, Tremont, IL (US)

(73) Assignee: Precision Planting LLC, Tremont, IL (US)

( * ) Notice: Subject to any disclaimer, the term of this patent is extended or adjusted under 35 U.S.C. 154(b) by 392 days.

(21) Appl. No.: 17/633,553

(22) PCT Filed: Jul. 9, 2020

(86) PCT No.: PCT/IB2020/056464
§ 371 (c)(1),
(2) Date: Feb. 7, 2022

(87) PCT Pub. No.: WO2021/024050
PCT Pub. Date: Feb. 11, 2021

(65) Prior Publication Data
US 2022/0346304 A1 Nov. 3, 2022

Related U.S. Application Data

(60) Provisional application No. 62/882,802, filed on Aug. 5, 2019.

(51) Int. Cl.
*A01B 79/00* (2006.01)
*A01B 79/02* (2006.01)
(Continued)

(52) U.S. Cl.
CPC ............. *A01B 79/02* (2013.01); *A01C 7/06* (2013.01); *A01C 7/102* (2013.01); *A01C 7/203* (2013.01);
(Continued)

(58) Field of Classification Search
CPC .......... A01B 79/02; A01C 7/06; A01C 7/102; A01C 7/203; G01N 33/246; G01N 2033/245
(Continued)

(56) References Cited

U.S. PATENT DOCUMENTS

| 4,293,295 A | 3/1981 | Knepper |
| 4,527,381 A | 7/1985 | Mann |

(Continued)

FOREIGN PATENT DOCUMENTS

| CA | 3 055 522 | 5/2020 |
| JP | 2019016010 A | 1/2019 |

(Continued)

OTHER PUBLICATIONS

UK Intellectual Property Office, Search Report Prepareed for related UK Application No. GB2000395.0, dated Jun. 26, 2020.
(Continued)

*Primary Examiner* — Tiffany P Young

(57) ABSTRACT

Speed control of machines and associated implements during transitions of agricultural parameters is described herein. In one embodiment, a processing system comprises processing logic to execute instructions for processing agricultural data and performing speed control of a machine and associated implement during a transition period for adjusting a setting of an agricultural parameter. A communication unit is coupled to the processing logic. The communication unit to transmit and receive data from the implement. The processing logic is configured to execute instructions to adjust the setting of the agricultural parameter and to determine a desired speed control during the transition period based on at least one of a desired transition distance and productivity during the transition period.

19 Claims, 9 Drawing Sheets

(51) Int. Cl.
- *A01C 7/00* (2006.01)
- *A01C 7/06* (2006.01)
- *A01C 7/10* (2006.01)
- *A01C 7/20* (2006.01)
- *G01N 33/24* (2006.01)

(52) U.S. Cl.
CPC ......... *G01N 33/246* (2013.01); *G01N 33/245* (2024.05)

(58) Field of Classification Search
USPC .......................................................... 701/50
See application file for complete search history.

(56) References Cited

U.S. PATENT DOCUMENTS

| | | |
|---|---|---|
| 6,918,342 B2 | 7/2005 | Sauder et al. |
| 8,789,482 B2 | 7/2014 | Garner et al. |
| 8,985,037 B2 | 3/2015 | Radtke et al. |
| 9,434,252 B2 | 9/2016 | Heindl |
| 10,034,425 B2 | 7/2018 | Ducroquet et al. |
| 10,111,380 B2 | 10/2018 | Long et al. |
| 10,257,979 B2 | 4/2019 | Walter |
| 10,308,116 B2 | 6/2019 | Czapka et al. |
| 2010/0180695 A1 | 7/2010 | Sauder et al. |
| 2014/0336818 A1 | 11/2014 | Posselius et al. |
| 2018/0208058 A1 | 7/2018 | Czapka et al. |
| 2020/0084953 A1* | 3/2020 | Stanhope .............. G01N 33/24 |
| 2020/0107488 A1* | 4/2020 | Schoeny ................ A01C 5/068 |

FOREIGN PATENT DOCUMENTS

| | | |
|---|---|---|
| WO | 2012/129442 A2 | 9/2012 |
| WO | 2012/149415 A1 | 11/2012 |
| WO | 2014/066664 A1 | 5/2014 |
| WO | 2017/143121 A1 | 8/2017 |
| WO | 2017/143125 A1 | 8/2017 |
| WO | 2020/039782 A1 | 2/2020 |
| WO | WO-2020227608 A1 * | 11/2020 ........... A01C 21/005 |

OTHER PUBLICATIONS

European Patent Office, International Search Report for related International Application No. PCT/IB2020/056464, mail date Oct. 8, 2020.

* cited by examiner

SPEED CONTROL OF IMPLEMENTS DURING TRANSITIONS OF SETTINGS OF AGRICULTURAL PARAMETERS

TECHNICAL FIELD

Embodiments of the present disclosure relate to speed control of machines and associated implements during transitions of settings of agricultural parameters.

BACKGROUND

Conventional control systems for planters typically require an operator to manually adjust one or more operating parameters of the planter to control desired spacing and depth of seeds being deposited by the planter. Operator error or inexperience can cause reduced planting productivity.

BRIEF DESCRIPTION OF THE DRAWINGS

The present disclosure is illustrated by way of example, and not by way of limitation, in the figures of the accompanying drawings and in which.

BRIEF SUMMARY

Speed control of machines and associated implements during transitions of settings of agricultural parameters is described herein. In one embodiment, a processing system comprises processing logic to execute instructions for processing agricultural data and performing speed control of a machine and associated implement during a transition period for adjusting a setting of an agricultural parameter. A communication unit is coupled to the processing logic. The communication unit to transmit and receive data from the implement. The processing logic is configured to execute instructions to adjust the setting of the agricultural parameter and to determine a desired speed control during the transition period based on a desired transition distance and productivity during the transition period.

DETAILED DESCRIPTION

Depth Control and Soil Monitoring Systems

Figure 1:
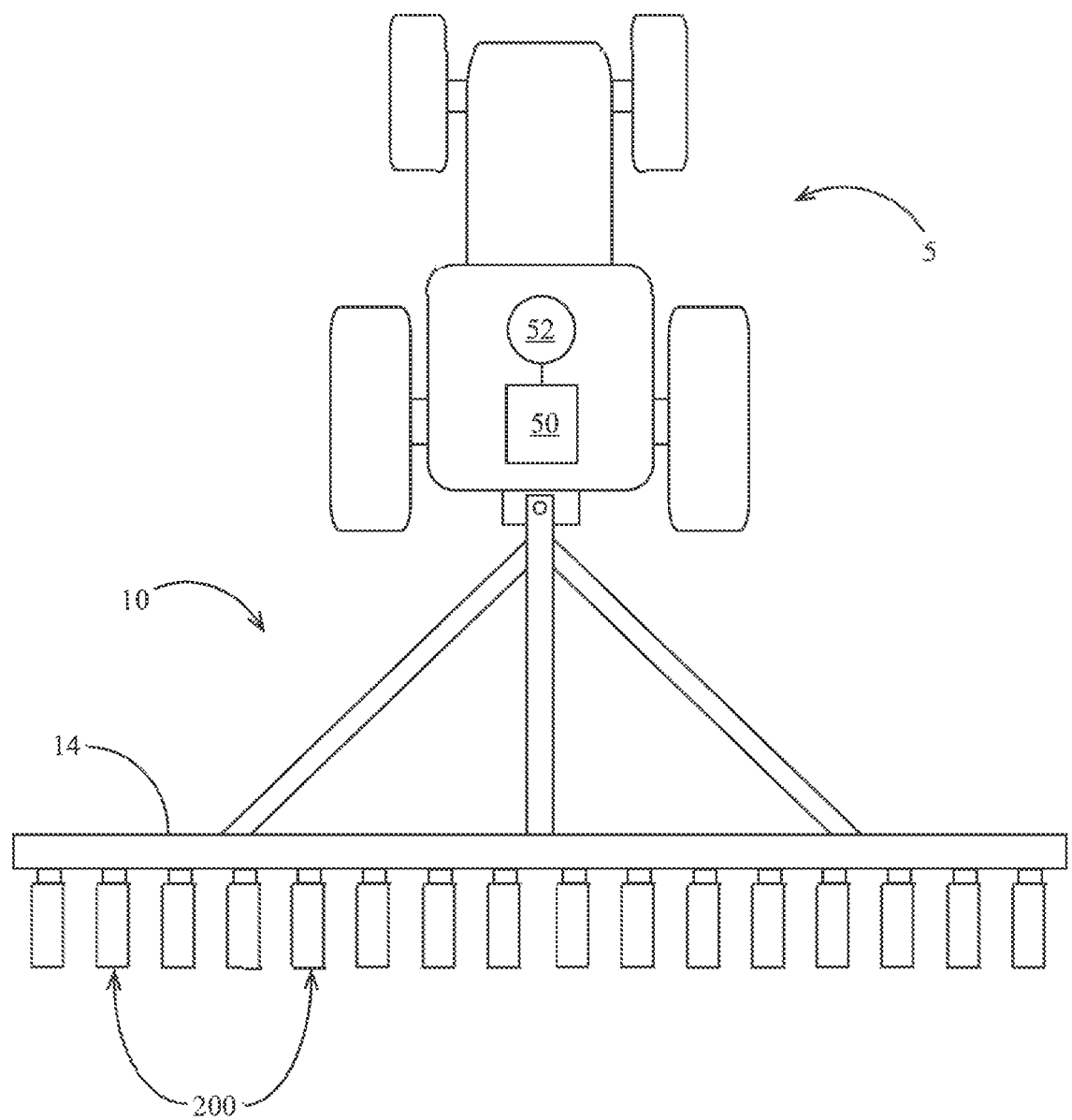
FIG. 1 is a top view of an embodiment of an agricultural planter.

Referring now to the drawings, wherein like reference numerals designate identical or corresponding parts throughout the several views, FIG. 1 illustrates a tractor 5 drawing an agricultural implement, e.g., a planter 10, comprising a toolbar 14 operatively supporting multiple row units 200. An implement monitor 50 preferably including a central processing unit ("CPU"), memory and graphical user interface ("GUI") (e.g., a touch-screen interface) is preferably located in the cab of the tractor 5. A global positioning system ("GPS") receiver 52 is preferably mounted to the tractor 5. The monitor 50 can control a speed of the tractor and associated implement in general. The speed can be adjusted during transitions of settings of agricultural parameters based on a desired distance for a transition and productivity during this transition.

Figure 2:
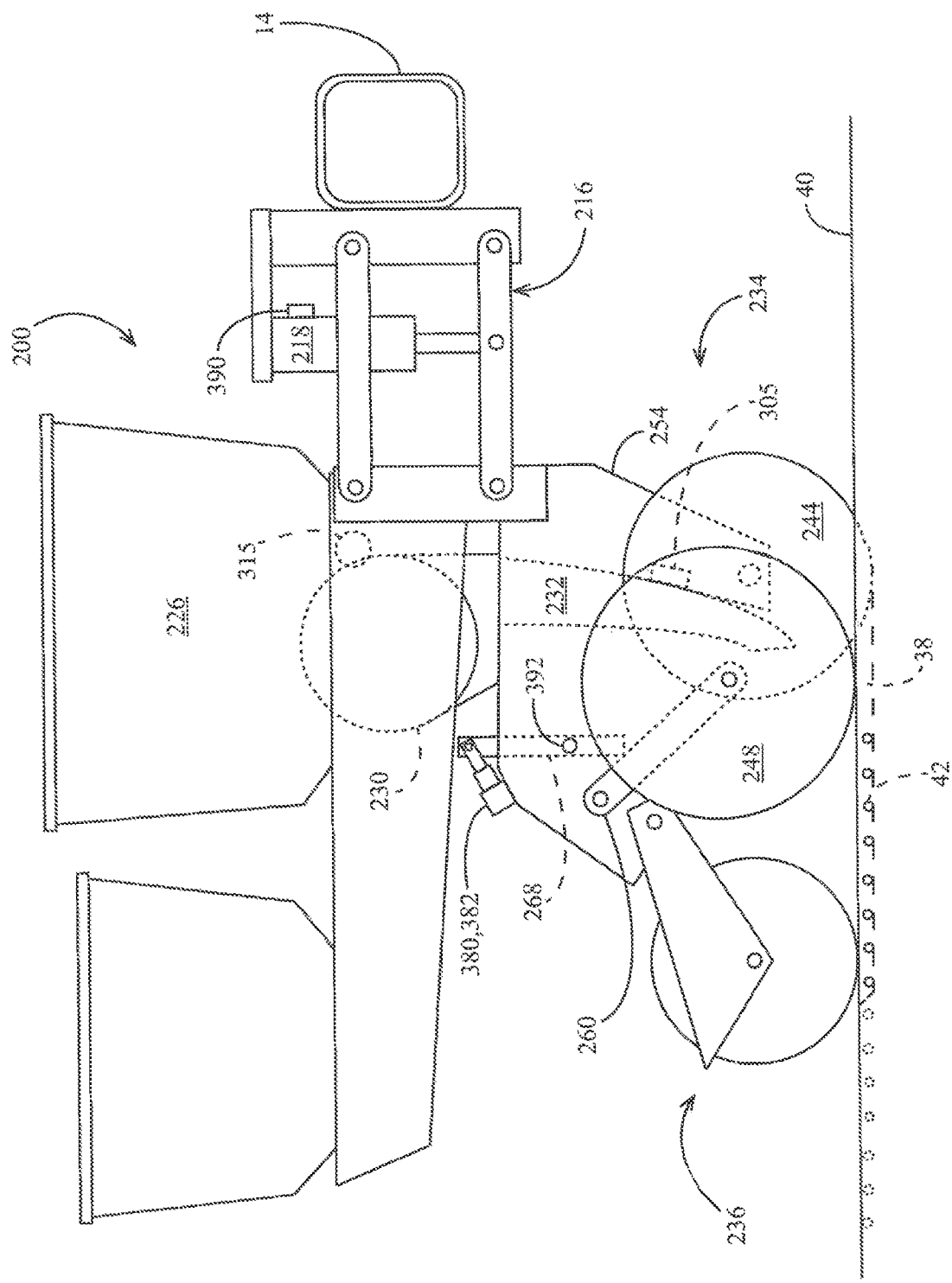
FIG. 2 is a side elevation view of an embodiment of a planter row unit.

Turning to FIG. 2, an embodiment is illustrated in which the row unit 200 is a planter row unit. The row unit 200 is preferably pivotally connected to the toolbar 14 by a parallel linkage 216. An actuator 218 is preferably disposed to apply lift and/or downforce on the row unit 200. A solenoid valve 390 is preferably in fluid communication with the actuator 218 for modifying the lift and/or downforce applied by the actuator. An opening system 234 preferably includes two opening discs 244 rollingly mounted to a downwardly-extending shank 254 and disposed to open a v-shaped trench 38 in the soil 40. A pair of gauge wheels 248 is pivotally supported by a pair of corresponding gauge wheel arms 260; the height of the gauge wheels 248 relative to the opener discs 244 sets the depth of the trench 38. A depth adjustment rocker 268 limits the upward travel of the gauge wheel arms 260 and thus the upward travel of the gauge wheels 248. A depth adjustment actuator 380 is preferably configured to modify a position of the depth adjustment rocker 268 and thus the height of the gauge wheels 248. The actuator 380 is preferably a linear actuator mounted to the row unit 200 and pivotally coupled to an upper end of the rocker 268. In some embodiments the depth adjustment actuator 380 comprises a device such as that disclosed in International Patent Application No. PCT/US2012/035585 ("the '585 application") or International Patent Application Nos. PCT/US2017/018269 or PCT/US2017/018274, the disclosure of each is hereby incorporated herein by reference. An encoder 382 is preferably configured to generate a signal related to the linear extension of the actuator 380; it should be appreciated that the linear extension of the actuator 380 is related to the depth of the trench 38 when the gauge wheel arms 260 are in contact with the rocker 268. A downforce sensor 392 is preferably configured to generate a signal related to the amount of force imposed by the gauge wheels 248 on the soil 40; in some embodiments the downforce sensor 392 comprises an instrumented pin about which the rocker 268 is pivotally coupled to the row unit 200, such as those instrumented pins disclosed in Applicant's U.S. patent application Ser. No. 12/522,253 (Pub. No. US 2010/0180695), the disclosure of which is hereby incorporated herein by reference.

Continuing to refer to FIG. 2, a seed meter 230 such as that disclosed in Applicant's International Patent Application No. PCT/US2012/030192, the disclosure of which is hereby incorporated herein by reference, is preferably disposed to deposit seeds 42 from a hopper 226 into the trench 38, e.g., through a seed tube 232 disposed to guide the seeds toward the trench. In some embodiments, instead of a seed tube 232, a seed conveyor is implemented to convey seeds from the seed meter to the trench at a controlled rate of speed as disclosed in U.S. patent application Ser. No. 14/347,902 and/or U.S. Pat. No. 8,789,482, both of which are incorporated by reference herein. In such embodiments, a bracket such as that shown in FIG. 30 is preferably configured to mount the seed firmer to the shank via sidewalls extending laterally around the seed conveyor, such that the seed firmer is disposed behind the seed conveyor to firm seeds into the soil after they are deposited by the seed conveyor. In some embodiments, the meter is powered by an electric drive 315 configured to drive a seed disc within the seed meter. In other embodiments, the drive 315 may comprise a hydraulic drive configured to drive the seed disc. A seed sensor 305 (e.g., an optical or electromagnetic seed sensor configured to generate a signal indicating passage of a seed) is preferably mounted to the seed tube 232 and disposed to send light or electromagnetic waves across the path of seeds 42. A closing system 236 including one or more closing wheels is pivotally coupled to the row unit 200 and configured to close the trench 38.

Figure 3:
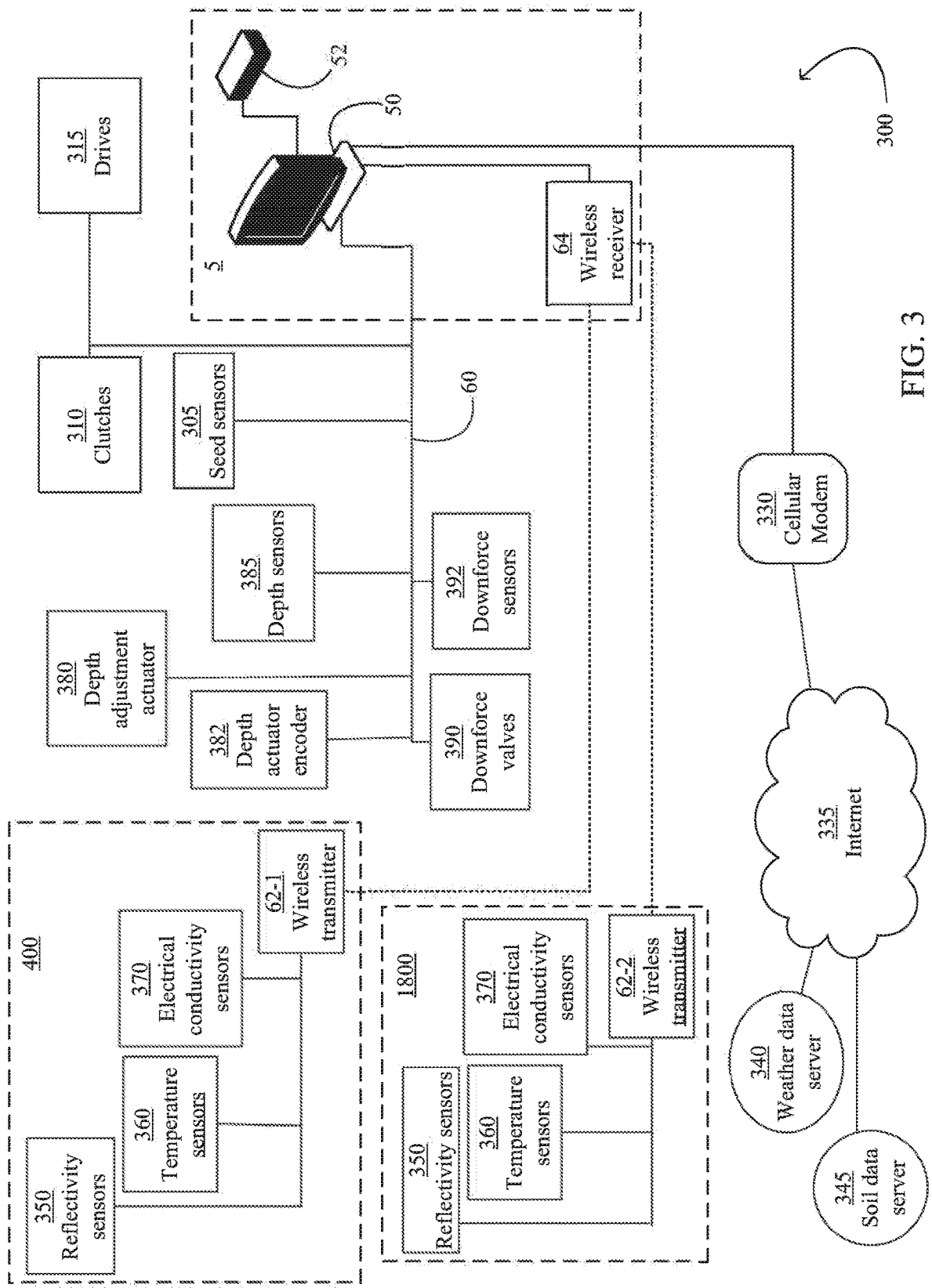
FIG. 3 schematically illustrates an embodiment of a soil monitoring system.

Turning to FIG. 3, a depth control and soil monitoring system 300 is schematically illustrated. The monitor 50 is preferably in data communication with components associated with each row unit 200 including the drives 315, the seed sensors 305, the GPS receiver 52, the downforce sensors 392, the valves 390, the depth adjustment actuator 380, and the depth actuator encoders 382. In some embodiments, particularly those in which each seed meter 230 is not driven by an individual drive 315, the monitor 50 is also preferably in data communication with clutches 310 configured to selectively operably couple the seed meter 230 to the drive 315.

Continuing to refer to FIG. 3, the monitor 50 is preferably in data communication with a cellular modem 330 or other component configured to place the monitor 50 in data communication with the Internet, indicated by reference numeral 335. The internet connection may comprise a wireless connection or a cellular connection. Via the Internet connection, the monitor 50 preferably receives data from a weather data server 340 and a soil data server 345. Via the Internet connection, the monitor 50 preferably transmits measurement data (e.g., measurements described herein) to a recommendation server (which may be the same server as the weather data server 340 and/or the soil data server 345) for storage and receives agronomic recommendations (e.g., planting recommendations such as planting depth, whether to plant, which fields to plant, which seed to plant, or which crop to plant) from a recommendation system stored on the server; in some embodiments, the recommendation system updates the planting recommendations based on the measurement data provided by the monitor 50.

Continuing to refer to FIG. 3, the monitor 50 is also preferably in data communication with one or more temperature sensors 360 mounted to the planter 10 and configured to generate a signal related to the temperature of soil being worked by the planter row units 200. The monitor 50 is preferably in data communication with one or more reflectivity sensors 350 mounted to the planter 10 and configured to generate a signal related to the reflectivity of soil being worked by the planter row units 200.

Referring to FIG. 3, the monitor 50 is preferably in data communication with one or more electrical conductivity sensors 365 mounted to the planter 10 and configured to generate a signal related to the temperature of soil being worked by the planter row units 200.

In some embodiments, a first set of reflectivity sensors 350, temperature sensors 360, and electrical conductivity sensors are mounted to a seed firmer 400 and disposed to measure reflectivity, temperature and electrical conductivity, respectively, of soil in the trench 38. In some embodiments, a second set of reflectivity sensors 350, temperature sensors 360, and electrical conductivity sensors 370 are mounted to a reference sensor assembly 1800 and disposed to measure reflectivity, temperature and electrical conductivity, respectively, of the soil, preferably at a depth different than the sensors on the seed firmer 400.

In some embodiments, a subset of the sensors are in data communication with the monitor 50 via a bus 60 (e.g., a CAN bus). In some embodiments, the sensors mounted to the seed firmer 400 and the reference sensor assembly 1800 are likewise in data communication with the monitor 50 via the bus 60. However, in the embodiment illustrated in FIG. 3, the sensors mounted to the seed firmer the sensors mounted to the seed firmer 400 and the reference sensor assembly 1800 are in data communication with the monitor 50 via a first wireless transmitter 62-1 and a second wireless transmitter 62-2, respectively. The wireless transmitters 62 at each row unit are preferably in data communication with a single wireless receiver 64 which is in turn in data communication with the monitor 50. The wireless receiver may be mounted to the toolbar 14 or in the cab of the tractor 5.

a. Soil Monitoring, Seed Monitoring and Seed Firming Apparatus

Figure 4:
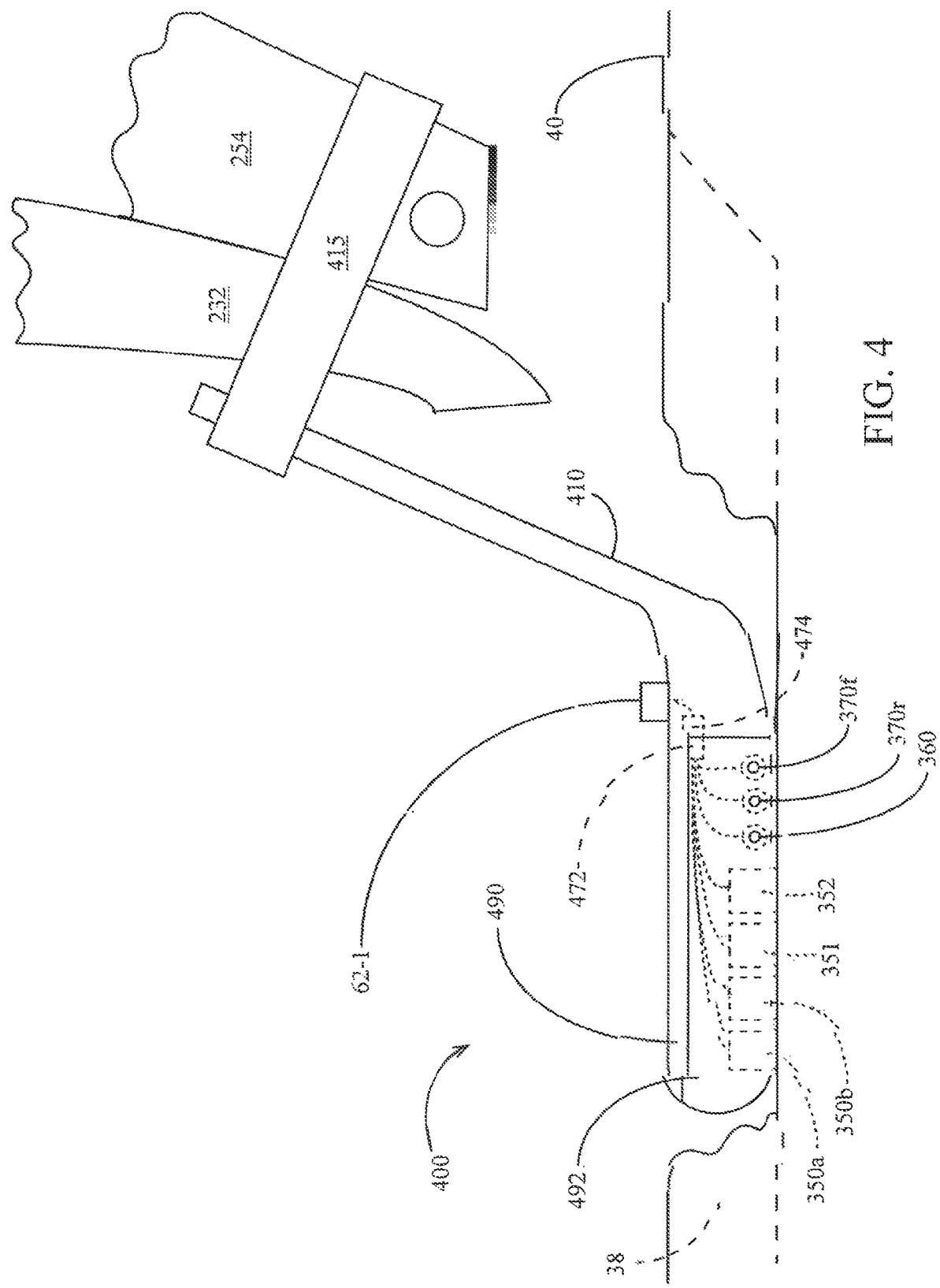
FIG. 4 is a side elevation view of an embodiment of a seed firmer having a plurality of firmer-mounted sensors.

Turning to FIG. 4, an embodiment of a seed firmer 400 is illustrated having a plurality of sensors for sensing soil characteristics. The seed firmer 400 preferably includes a flexible portion 410 mounted to the shank 254 and/or the seed tube 232 by a bracket 415. In some embodiments, the bracket 415 is similar to one of the bracket embodiments disclosed in U.S. Pat. No. 6,918,342, incorporated by reference herein. The seed firmer preferably includes a firmer body 490 disposed and configured to be received at least partially within v-shaped trench 38 and firm seeds 42 into the bottom of the trench. When the seed firmer 400 is lowered into the trench 38, the flexible portion 410 preferably urges the firmer body 490 into resilient engagement with the trench. In some embodiments the flexible portion 410 preferably includes an external or internal reinforcement as disclosed in PCT/US2013/066652, incorporated by reference herein. In some embodiments the firmer body 490 includes a removable portion 492; the removable portion 492 preferably slides into locking engagement with the remainder of the firmer body. The firmer body 490 (preferably including the portion of the firmer body engaging the soil, which in some embodiments comprises the removable portion 492) is preferably made of a material (or has an outer surface or coating) having hydrophobic and/or anti-stick properties, e.g. having a Teflon graphite coating and/or comprising a polymer having a hydrophobic material (e.g., silicone oil or polyether-ether-ketone) impregnated therein. Alternatively, the sensors can be disposed on the side of seed firmer 400 (not shown).

Returning to FIGS. 4 and 5, the seed firmer 400 preferably includes a plurality of reflectivity sensors 350a, 350b. Each reflectivity sensor 350 is preferably disposed and configured to measure reflectivity of soil; in a preferred embodiment, the reflectivity sensor 350 is disposed to measure soil in the trench 38, and preferably at the bottom of the trench. The reflectivity sensor 350 preferably includes a lens disposed in the bottom of the firmer body 490 and disposed to engage the soil at the bottom of the trench 38. In some embodiments the reflectivity sensor 350 comprises one of the embodiments disclosed in U.S. Pat. No. 8,204,689 and/or U.S. Provisional Patent Application 61/824,975 ("the '975 application"), both of which are incorporated by reference herein. In various embodiments, the reflectivity sensor 350 is configured to measure reflectivity in the visible range (e.g., 400 and/or 600 nanometers), in the near-infrared range (e.g., 940 nanometers) and/or elsewhere the infrared range.

The seed firmer 400 may also include a capacitive moisture sensor 351 disposed and configured to measure capacitance moisture of the soil in the seed trench 38, and preferably at the bottom of trench 38.

The seed firmer 400 may also include an electronic tensiometer sensor 352 disposed and configured to measure soil moisture tension of the soil in the seed trench 38, and preferably at the bottom of trench 38.

Alternatively, soil moisture tension can be extrapolated from capacitive moisture measurements or from reflectivity measurements (such as at 1450 nm). This can be done using a soil water characteristic curve based on the soil type.

The seed firmer 400 may also include a temperature sensor 360. The temperature sensor 360 is preferably disposed and configured to measure temperature of soil; in a preferred embodiment, the temperature sensor is disposed to measure soil in the trench 38, preferably at or adjacent the bottom of the trench 38. The temperature sensor 360 preferably includes soil-engaging ears 364, 366 disposed to slidingly engage each side of the trench 38 as the planter traverses the field. The ears 364, 366 preferably engage the trench 38 at or adjacent to the bottom of the trench. The ears 364, 366 are preferably made of a thermally conductive material such as copper. The ears 364 are preferably fixed to and in thermal communication with a central portion 362 housed within the firmer body 490. The central portion 362 preferably comprises a thermally conductive material such as copper; in some embodiments the central portion 362 comprises a hollow copper rod. The central portion 362 is preferably in thermal communication with a thermocouple fixed to the central portion. In other embodiments, the temperature sensor 360 may comprise a non-contact temperature sensor such as an infrared thermometer. In some embodiments, other measurements made by the system 300 (e.g., reflectivity measurements, electrical conductivity measurements, and/or measurements derived from those measurements) are temperature-compensated using the temperature measurement made by the temperature sensor 360. The adjustment of the temperature-compensated measurement based on temperature is preferably carried out by consulting an empirical look-up table relating the temperature-compensated measurement to soil temperature. For example, the reflectivity measurement at a near-infrared wavelength may be increased (or in some examples, reduced) by 1% for every 1 degree Celsius in soil temperature above 10 degrees Celsius.

The seed firmer preferably includes a plurality of electrical conductivity sensors 370r, 370f. Each electrical conductivity sensor 370 is preferably disposed and configured to measure electrical conductivity of soil; in a preferred embodiment, the electrical conductivity sensor is disposed to measure electrical conductivity of soil in the trench 38, preferably at or adjacent the bottom of the trench 38. The electrical conductivity sensor 370 preferably includes soil-engaging ears 374, 376 disposed to slidingly engage each side of the trench 38 as the planter traverses the field. The ears 374, 376 preferably engage the trench 38 at or adjacent to the bottom of the trench. The ears 374, 376 are preferably made of a electrically conductive material such as copper. The ears 374 are preferably fixed to and in electrical communication with a central portion 372 housed within the firmer body 490. The central portion 372 preferably comprises an electrically conductive material such as copper; in some embodiments the central portion 372 comprises a copper rod. The central portion 372 is preferably in electrical communication with an electrical lead fixed to the central portion. The electrical conductivity sensor can measure the electrical conductivity within a trench by measuring the electrical current between soil-engaging ears 374 and 376.

Figure 5:
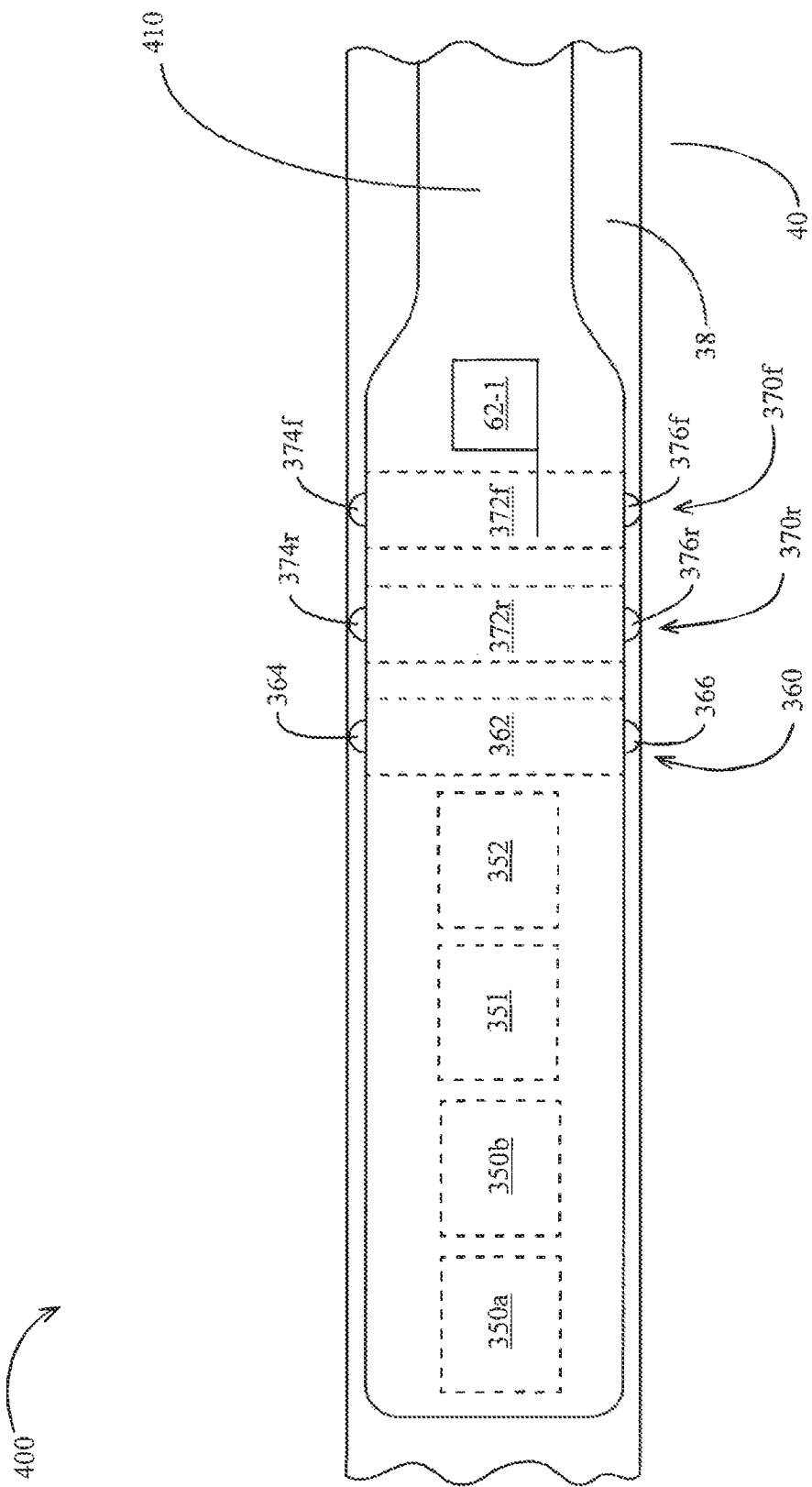
FIG. 5 illustrates an embodiment in which the system 300 measures electrical conductivity of soil adjacent the trench 38 by measuring an electrical potential between the forward electrical conductivity sensor 370f and the rearward electrical conductivity sensor 370f.

Referring to FIG. 5, in some embodiments the system 300 measures electrical conductivity of soil adjacent the trench 38 by measuring an electrical potential between the forward electrical conductivity sensor 370f and the rearward electrical conductivity sensor 370f. In other embodiments, the electrical conductivity sensors 370f, 370r may be disposed in longitudinally spaced relation on the bottom of the seed firmer in order to measure electrical conductivity at the bottom of the seed trench.

In other embodiments, the electrical conductivity sensors 370 comprise one or more ground-working or ground-contacting devices (e.g., discs or shanks) that contact the soil and are preferably electrically isolated from one another or from another voltage reference. The voltage potential between the sensors 370 or other voltage reference is preferably measured by the system 300. The voltage potential or another electrical conductivity value derived from the voltage potential is preferably and reported to the operator. The electrical conductivity value may also be associated with the GPS-reported position and used to generate a map of the spatial variation in electrical conductivity throughout the field. In some such embodiments, the electrical conductivity sensors may comprise one or more opening discs of a planter row unit, row cleaner wheels of a planter row unit, ground-contacting shanks of a planter, ground-contacting shoes depending from a planter shank, shanks of a tillage tool, or discs of a tillage tool. In some embodiments a first electrical conductivity sensor may comprise a component (e.g., disc or shank) of a first agricultural row unit while a second electrical conductivity sensor comprises a component (e.g., disc or shank) of a second agricultural row unit, such that electrical conductivity of soil extending transversely between the first and second row units is measured. It should be appreciated that at least one of the electrical conductivity sensors described herein is preferably electrically isolated from the other sensor or voltage reference. In one example, the electrical conductivity sensor is mounted to an implement (e.g., to the planter row unit or tillage tool) by being first mounted to an electrically insulating component (e.g., a component made from an electrically insulating material such as polyethylene, polyvinyl chloride, or a rubber-like polymer) which is in turn mounted to the implement.

In other embodiments, below is a table relating measured properties (some listed above), each of the property's impact on seed germination and/or emergence; how the property is measured; output of the information as raw data, seed environment score, time to germination, time to emergence, and/or seed germination risk; and actuation of equipment or action to take. Note, a Stop Planting Action may be listed below for a Measured Property for which Stop Planting alone may not be taken, but Stop Planting may be an action for this Measured Property in combination with one or more other Measured Properties. For example, soil color alone may not be a reason to stop planting, but soil color in combination with other Measured Properties may result in a Stop Planting Action. This can also be the situation for other actions, such as Row Cleaner Aggressiveness.

| Measured Property | Impact on germination/ emergence | How Measured | Output | Actuation/ Action |
|---|---|---|---|---|
| Soil Color | Radiative heat absorption | Seed firmer 400, 400' Imagery | Raw data<br>Days to Germination<br>Days to Emergence<br>Seed Germination Risk<br>Seed Environment Score | Adjust depth<br>Adjust downforce<br>Hybrid selection<br>Row cleaner aggressiveness<br>Stop planting |
| Residue | Radiative heat absorption<br>Residue in furrow<br>Seed environment quality | Seed firmer 400, 400' Imagery | Raw data<br>Days to Germination<br>Days to Emergence<br>Seed Germination Risk<br>Seed Environment Score | Row cleaner aggressiveness<br>Adjust depth<br>Adjust downforce |
| Topography | Watershed runoff or infiltration | Reference source | Raw data<br>Days to Germination<br>Days to Emergence<br>Seed Germination Risk<br>Seed Environment Score | Adjust depth<br>Adjust downforce<br>Row cleaner aggressiveness<br>Stop planting |
| Soil Texture/Type | Water holding capacity<br>Seed imbibing rate<br>Thermal insulative factor | Seed firmer 400, 400' Imagery | Raw data<br>Days to Germination<br>Days to Emergence<br>Seed Germination Risk<br>Seed Environment Score | Adjust depth<br>Adjust downforce<br>Hybrid selection<br>Row cleaner aggressiveness<br>Stop planting |
| Organic Matter | Water holding capacity<br>Seed imbibing rate<br>Thermal insulative factor | Seed firmer 400, 400' Imagery | Raw data<br>Days to Germination<br>Days to Emergence<br>Seed Germination Risk<br>Seed Environment Score | Adjust depth<br>Adjust downforce<br>Population<br>Hybrid selection<br>Row cleaner aggressiveness<br>Stop planting |
| Soil Temperature | Impact on germination | Seed firmer 400, 400' | Raw data<br>Days to Germination<br>Days to Emergence<br>Seed Germination Risk<br>Seed Environment Score | Adjust depth<br>Adjust downforce<br>Population<br>Stop planting<br>Row cleaner aggressiveness |
| Soil Moisture | Impact on germination | Seed firmer 400, 400' | Raw data<br>Days to Germination<br>Days to Emergence<br>Seed Germination Risk<br>Seed Environment Score | Adjust depth<br>Adjust downforce<br>Population<br>Stop planting<br>Row cleaner aggressiveness |
| Seed Shape/Size | Volume of water to germinate | User input | Raw data<br>Days to Germination<br>Days to Emergence<br>Seed Germination Risk<br>Seed Environment Score | Adjust depth<br>Adjust downforce<br>Hybrid selection<br>Row cleaner aggressiveness<br>Stop planting |
| Seed Cold Germ | Risk of no germination based on temperature | User input | Raw data<br>Days to Germination<br>Days to Emergence<br>Seed Germination Risk<br>Seed Environment Score | Adjust depth<br>Adjust downforce<br>Hybrid selection<br>Row cleaner aggressiveness<br>Stop planting |
| Time of Day | Bias of current temperature, moisture | Monitor | Raw data | N/A |
| Furrow Depth | Insulative effect of soil,<br>Time required to emerge from this depth | Depth Actuator/ Depth Sensor | Raw data<br>Days to Germination<br>Days to Emergence<br>Seed Germination Risk<br>Seed Environment Score | Adjust depth<br>Adjust downforce<br>Row cleaner aggressiveness<br>Stop planting |
| Temperature Forecast | Temperature impact on germination | Weather source | Raw data<br>Days to Germination<br>Days to Emergence<br>Seed Germination Risk<br>Seed Environment Score | Adjust depth<br>Adjust downforce<br>Population<br>Hybrid selection<br>Stop planting<br>Row cleaner aggressiveness |
| Precipitation Forecast | Moisture impact on germination | Weather source | Raw data<br>Days to Germination<br>Days to Emergence<br>Seed Germination Risk<br>Seed Environment Score | Adjust depth<br>Adjust downforce<br>Population<br>Hybrid selection<br>Stop planting<br>Row cleaner aggressiveness |

-continued

| Measured Property | Impact on germination/emergence | How Measured | Output | Actuation/Action |
|---|---|---|---|---|
| Wind Speed Forecast | Thermal and evaporative impact on soil temperature and/or moisture | Weather source | Raw data<br>Days to Germination<br>Days to Emergence<br>Seed Germination Risk<br>Seed Environment Score | Adjust depth<br>Adjust downforce<br>Population<br>Hybrid selection<br>Stop planting<br>Row cleaner aggressiveness |
| Cloud Cover Forecast | Thermal and evaporative impact on soil temperature and/or moisture | Weather source | Raw data<br>Days to Germination<br>Days to Emergence<br>Seed Germination Risk<br>Seed Environment Score | Adjust depth<br>Adjust downforce<br>Population<br>Hybrid selection<br>Stop planting<br>Row cleaner aggressiveness |

In other embodiments, any of the sensors do not need to be disposed in a firmer. The sensors can be in any implement that is disposed on an agricultural implement in contact with the soil. For example, firmer body 490 can be mounted to any bracket and disposed anywhere on an agricultural implement and in contact with soil. Examples of an agricultural implement include, but are not limited to, planters, harvesters, sprayers, side dress bars, tillers, fertilizer spreaders, and tractor.

There are many ways of handling transitions of settings of agricultural parameters. For example, for multihybrid, there is a planned exhaustion of seeds from the seed meter before making a switch to the different seed type. In general, when a change is needed, the change is commanded, but without slowing of the tractor to reduce the transition zone. The monitor/controller is connected to the tractor over a CAN/ISOBUS network and control tractor speed.

There exists some mechanical systems that have a maximum actuation speed when changing from a first setpoint to a second setpoint for an agricultural parameter (e.g., soil properties, moisture, seed depth, seed population, multihybrid change from one type of hybrid to another, liquid/granular fertilizer/insecticide/herbicide/fungicide application, tillage depth for different compaction zones). When knowledge of a setpoint change exists prior to execution of the change, actuation for the setpoint change can occur proactively, ensuring that the target is reached at the intended point in time.

In other cases, knowledge of a setpoint change is not known ahead of time.

As a result, the setpoint changes in a reactionary fashion, and a period of time exists in which the setpoint and actual are different. On an agricultural implement, this transition zone appears as a distance within a field, where the distance is proportional to the time required to complete actuation.

If implement speed can be controlled, speed can be reduced during a transition, shortening the transition zone.

Figure 6:
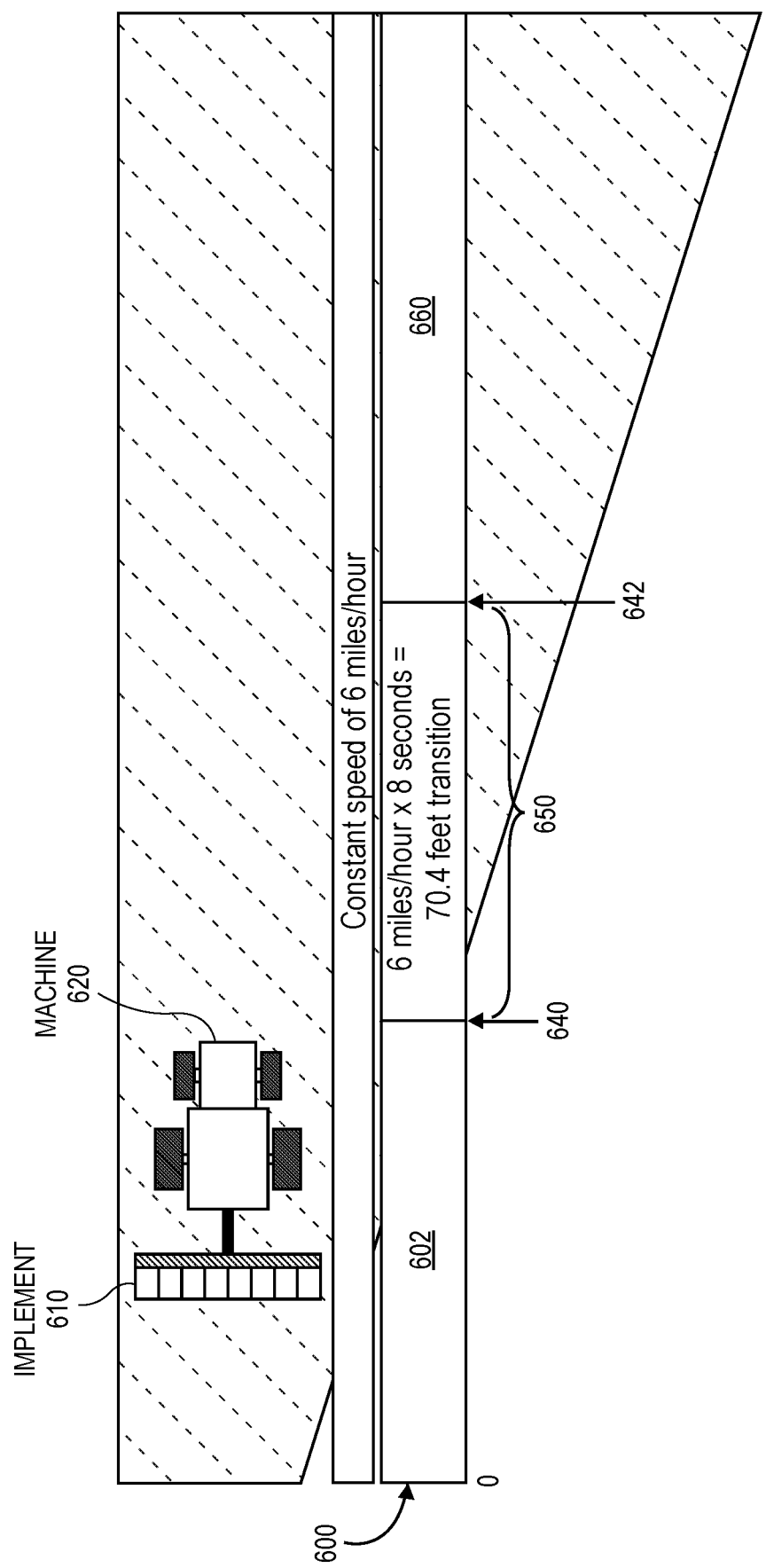
FIG. 6 illustrates a timeline 600 for adjusting an agricultural parameter during planting with no speed adjustment of a machine 620.

FIG. 6 illustrates a timeline 600 for adjusting a setting of an agricultural parameter during planting with no speed adjustment of a machine 620. The machine 620 is pulling an implement 610 through an agricultural field. In one example, the machine has a constant speed (e.g., 6 mph), a ⅛" per second maximum actuation rate for changing a depth setting of the implement from a first setpoint (e.g., 1" depth) during time period 602 to a second setpoint (e.g., 2" depth) for time period 660. A transition period 650 from time 640 to time 642 occurs for this change from the first setpoint to the second setpoint. In this example, the transition period 650 lasts for 8 seconds and corresponds to a 70.4 ft transition in the field. No speed adjustment is performed during the transition period 650.

Figure 7:
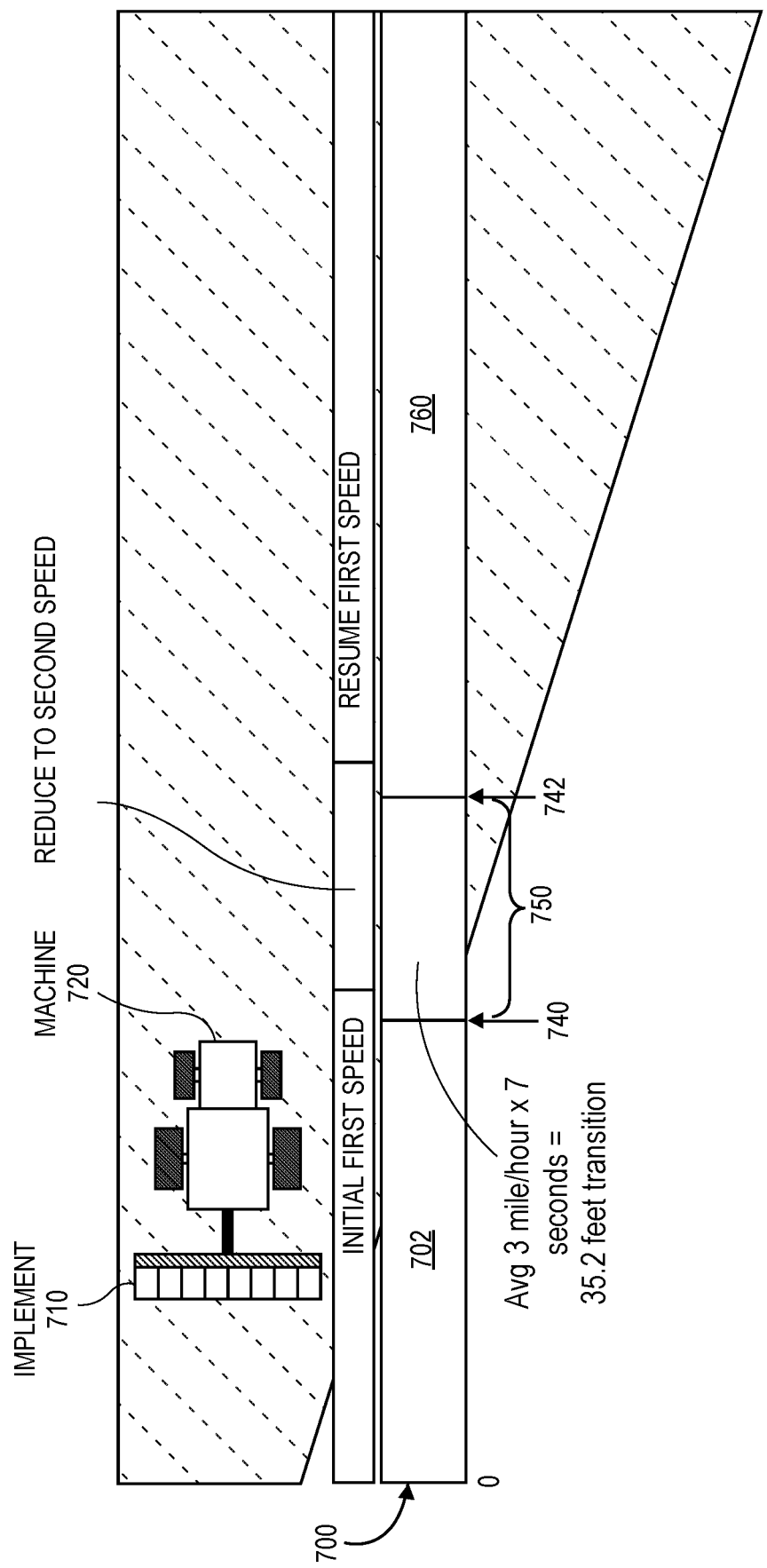
FIG. 7 illustrates a timeline 700 for adjusting an agricultural parameter during planting with speed adjustment of a machine 720 in accordance with one embodiment.

FIG. 7 illustrates a timeline 700 for adjusting a setting of an agricultural parameter with speed adjustment of a machine 720 in accordance with one embodiment. The machine 720 is pulling an implement 710 through an agricultural field. In one example, the machine has an adjustable speed (e.g., 3-10 mph) that adjusts during a transition time period, a ⅛" per second maximum actuation rate for changing a depth setting of the implement from a first setpoint (e.g., 1" depth) during time period 702 to a second setpoint (e.g., 2" depth) for time period 760. A transition period 750 from time 740 to time 742 occurs for this change from the first setpoint to the second setpoint. In this example, the transition period 750 lasts for 8 seconds and corresponds to a 35.2 ft transition in the field. The machine speed is reduced from an initial speed for time period 702 to a second speed (e.g., 3 mph) during the transition period 750, and then increases to the first speed (or a different speed) during time period 760.

Figure 8:
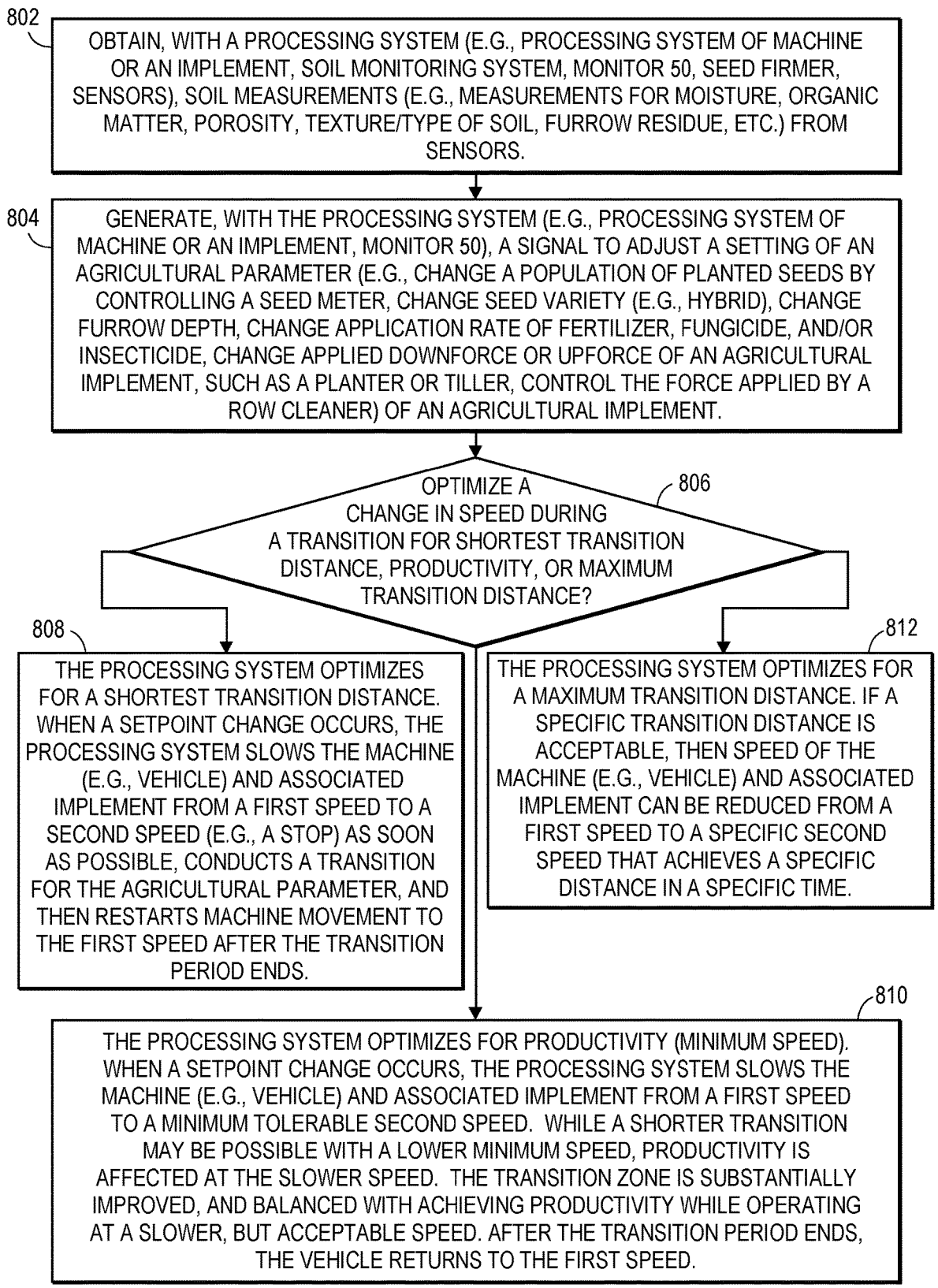
FIG. 8 illustrates a flow diagram of one embodiment for a method 800 of obtaining soil measurements and then generating a signal to actuate any implement on any agricultural implement.

FIG. 8 illustrates a flow diagram of one embodiment for a method 800 of using speed control of implements during transitions of agricultural parameters to optimize these transitions. The method 800 is performed by hardware (circuitry, dedicated logic, etc.), software (such as is run on a general purpose computer system or a dedicated machine or a device), or a combination of both. In one embodiment, the method 800 is performed by at least one system or device (e.g., monitor 80, processing system of a machine, processing system of an implement, soil monitoring system, seed firmer, sensors, implement, row unit, etc). The system executes instructions of a software application or program with processing logic. The software application or program can be initiated by a system or may notify an operator or user of a machine (e.g., tractor, planter, combine) depending on whether agricultural conditions cause a signal to actuate an implement. In one example, a machine pulls an implement in an agricultural field.

In any embodiment herein, at operation 802, a processing system (e.g., processing system of machine or an implement, soil monitoring system, monitor 50, seed firmer, sensors) can optionally obtain soil measurements (e.g., measurements for moisture, organic matter, porosity, texture/type of soil, furrow residue, etc.) from sensors. At operation 804, the processing system (e.g., processing system of machine or an implement, monitor 50) can generate a signal to adjust a setting of an agricultural parameter (e.g., change a population of planted seeds by controlling a seed meter, change seed variety (e.g., hybrid), change furrow depth, change application rate of fertilizer, fungicide, and/or insecticide, change applied downforce or upforce of an agricultural implement, such as a planter or tiller, control the force applied by a row cleaner) of an agricultural implement. Generating a signal to actuate an agricultural parameter may be in response to obtaining soil measurements from soil sensors or data obtained from other sensors. This can be done in real time on the go. Examples of soil measurements that can be measured and the control of implements include, but are not limited to:

A) moisture, organic matter, porosity, or texture/type of soil to change a population of planted seeds by controlling a seed meter;

B) moisture, organic matter, porosity, or texture/type of soil to change seed variety (e.g., hybrid);

C) moisture, organic matter, porosity, or texture/type of soil to change furrow depth:

D) moisture, organic matter, porosity, or texture/type of soil to change application rate of fertilizer, fungicide, and/or insecticide;

E) moisture, organic matter, porosity, or texture/type of soil to change applied downforce or upforce of an agricultural implement, such as a planter or tiller;

F) furrow residue to control the force applied by a row cleaner.

In one embodiment for downforce or upforce, a combination of moisture and texture/type can be used. Higher downforce can be applied in sandy and/or wet soils, and lower downforce can be used in clay and/or wet soils. Too much downforce for a given soil type can cause compaction of the soil, which decreases the ability of roots to spread throughout the soil. Too little downforce for a given soil type can allow an implement to ride up and not plant seeds to a targeted depth. The downforce is generally applied through the gauge wheels 248 adjacent to the trench.

At operation 806, upon detection of adjustment of the agricultural parameter (or having knowledge of an adjustment of the agricultural parameter prior to the actual adjustment), the processing system determines whether to optimize a change in speed for a machine and associated agricultural implement during a transition period for shortest transition distance, productivity, or maximum transition distance. At operation 808, the processing system optimizes for a shortest transition distance. When a setpoint change occurs, the processing system slows the machine (e.g., vehicle) and associated implement from a first speed to a second speed (e.g., a stop) as soon as possible, conducts a transition for the agricultural parameter, and then restarts machine movement to the first speed (or a different speed) after the transition period ends.

At operation 810, the processing system optimizes for productivity (minimum speed). When a setpoint change occurs, the processing system slows the machine (e.g., vehicle) and associated implement from a first speed to a minimum tolerable second speed. While a shorter transition may be possible with a lower minimum speed, productivity is affected at the slower speed. The transition zone is substantially improved, and balanced with achieving productivity while operating at a slower, but acceptable speed. After the transition period ends, the vehicle returns to the first speed.

At operation 812, the processing system optimizes for a maximum transition distance. If a specific transition distance is acceptable, then speed of the machine (e.g., vehicle) and associated implement can be reduced from a first speed to a specific second speed that achieves a specific distance in a specific time. For example, if a 50 ft transition is acceptable, and 10 seconds are required to transition, then the speed need not be reduced below 5 feet/second during the transition period.

Controlling tractor speed can provide a means to shorten (in distance) a transition. In one example, an algorithm determines when Amoisture/Adistance increases, then this algorithm signals that an implement is transitioning between zones, and the processing restricts speed based on a magnitude of a zone transition for a length of the transition.

In another example, if an implement enters a region with above normal moisture volatility (based on knowledge from adjacent neighboring passes through a field), speed is temporarily restricted while in the region to ensure that any transitions occur with a shorter response distance, and speed restrictions are removed once leaving the region.

Figure 9:
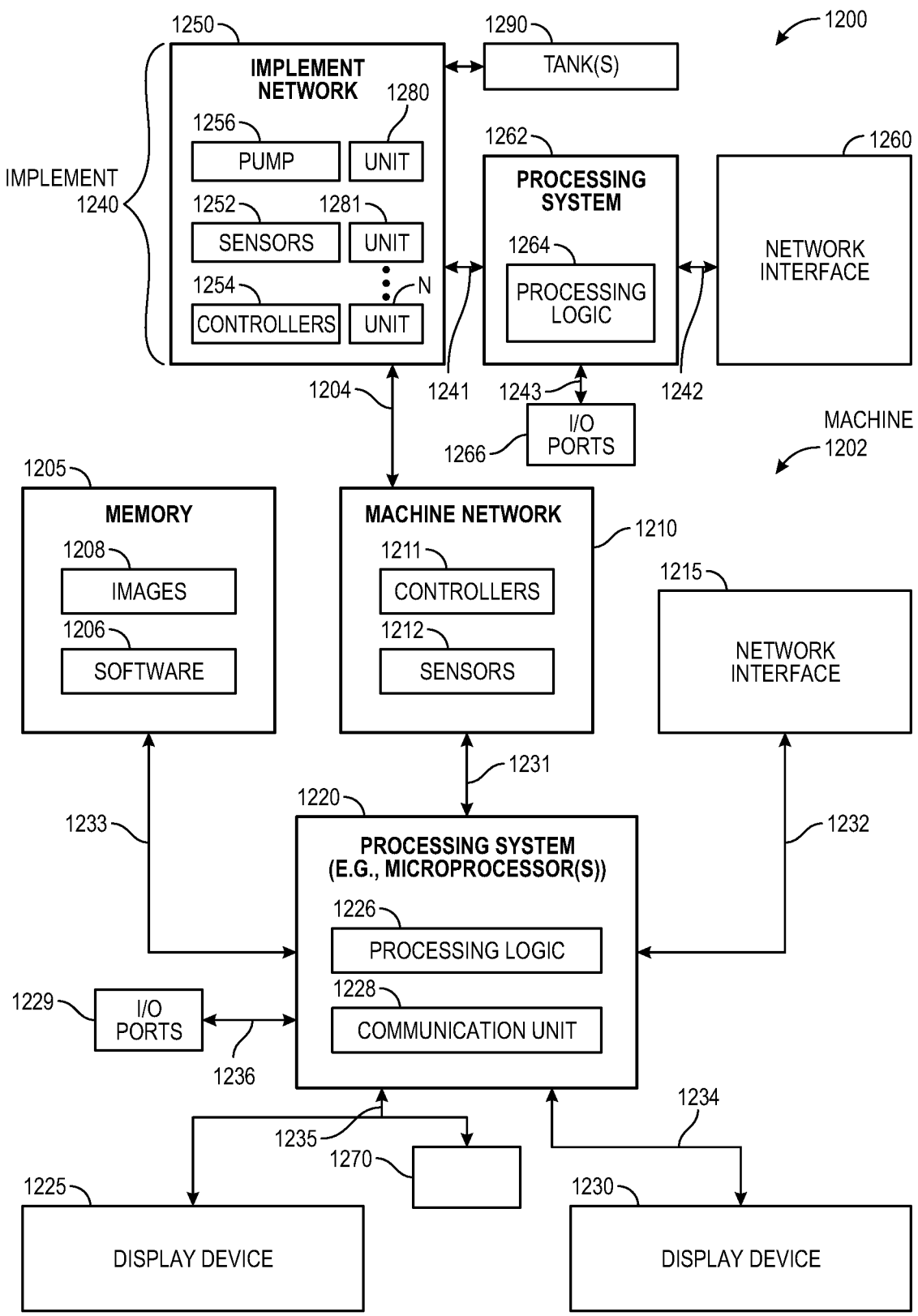
FIG. 9 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment.

FIG. 9 shows an example of a system 1200 that includes a machine 1202 (e.g., tractor, combine harvester, etc.) and an implement 1240 (e.g., planter, sidedress bar, cultivator, plough, sprayer, spreader, irrigation implement, etc.) in accordance with one embodiment. The machine 1202 includes a processing system 1220, memory 1205, machine network 1210 (e.g., a controller area network (CAN) serial bus protocol network, an ISOBUS network, etc.), and a network interface 1215 for communicating with other systems or devices including the implement 1240. The machine network 1210 includes sensors 1212 (e.g., speed sensors), controllers 1211 (e.g., GPS receiver, radar unit) for controlling and monitoring operations of the machine or implement. The network interface 1215 can include at least one of a GPS transceiver, a WLAN transceiver (e.g., WiFi), an infrared transceiver, a Bluetooth transceiver, Ethernet, or other interfaces from communications with other devices and systems including the implement 1240. The network interface 1215 may be integrated with the machine network 1210 or separate from the machine network 1210 as illustrated in FIG. 12. The I/O ports 1229 (e.g., diagnostic/on board diagnostic (OBD) port) enable communication with another data processing system or device (e.g., display devices, sensors, etc.).

In one example, the machine performs operations of a tractor that is coupled to an implement for planting applications of a field. The planting data for each row unit of the implement can be associated with locational data at time of application to have a better understanding of the planting for each row and region of a field. Data associated with the planting applications can be displayed on at least one of the display devices 1225 and 1230. The display devices can be integrated with other components (e.g., processing system 1220, memory 1205, etc.) to form the monitor 50.

The processing system 1220 may include one or more microprocessors, processors, a system on a chip (integrated circuit), or one or more microcontrollers. The processing system includes processing logic 1226 for executing software instructions of one or more programs and a communication unit 1228 (e.g., transmitter, transceiver) for transmitting and receiving communications from the machine via machine network 1210 or network interface 1215 or implement via implement network 1250 or network interface 1260. The communication unit 1228 may be integrated with the processing system or separate from the processing system. In one embodiment, the communication unit 1228 is in data communication with the machine network 1210 and implement network 1250 via a diagnostic/OBD port of the I/O ports 1229.

Processing logic 1226 including one or more processors or processing units may process the communications received from the communication unit 1228 including agricultural data (e.g., GPS data, planting application data, soil characteristics, any data sensed from sensors of the implement 1240 and machine 1202, etc.). The system 1200 includes memory 1205 for storing data and programs for execution (software 1206) by the processing system. The memory 1205 can store, for example, software components such as speed control software for optimizing speed control during a transition of a setpoint of an agricultural parameter (e.g., method 800), as planting application software for analysis of soil and planting applications for performing operations of the present disclosure, or any other software application or module, images (e.g., captured images of crops, soil, furrow, soil clods, row units, etc.), alerts, maps, etc. The memory 1205 can be any known form of a machine readable non-transitory storage medium, such as semiconductor memory (e.g., flash; SRAM; DRAM; etc.) or non-volatile memory, such as hard disks or solid-state drive. The system can also include an audio input/output subsystem (not shown) which may include a microphone and a speaker for, for example, receiving and sending voice commands or for user authentication or authorization (e.g., biometrics).

The processing system 1220 communicates bi-directionally with memory 1205, machine network 1210, network interface 1215, header 1280, display device 1230, display device 1225, and I/O ports 1229 via communication links 1231-1236, respectively. The processing system 1220 can be integrated with the memory 1205 or separate from the memory 1205.

Display devices 1225 and 1230 can provide visual user interfaces for a user or operator. The display devices may include display controllers. In one embodiment, the display device 1225 is a portable tablet device or computing device with a touchscreen that displays data (e.g., speed control data, planting application data, captured images, localized view map layer, high definition field maps of seed germination data, seed environment data, as-planted or as-harvested data or other agricultural variables or parameters, yield maps, alerts, etc.) and data generated by an agricultural data analysis software application and receives input from the user or operator for an exploded view of a region of a field, monitoring and controlling field operations. The operations may include configuration of the machine or implement, reporting of data, control of the machine or implement including sensors and controllers, and storage of the data generated. The display device 1230 may be a display (e.g., display provided by an original equipment manufacturer (OEM)) that displays images and data for a localized view map layer, as-applied fluid application data, as-planted or as-harvested data, yield data, seed germination data, seed environment data, controlling a machine (e.g., planter, tractor, combine, sprayer, etc.), steering the machine, and monitoring the machine or an implement (e.g., planter, combine, sprayer, etc.) that is connected to the machine with sensors and controllers located on the machine or implement.

A cab control module 1270 may include an additional control module for enabling or disabling certain components or devices of the machine or implement. For example, if the user or operator is not able to control the machine or implement using one or more of the display devices, then the cab control module may include switches to shut down or turn off components or devices of the machine or implement.

The implement 1240 (e.g., planter, cultivator, plough, sprayer, spreader, irrigation implement, etc.) includes an implement network 1250, a processing system 1262, a network interface 1260, and optional input/output ports 1266 for communicating with other systems or devices including the machine 1202. The implement network 1250 (e.g, a controller area network (CAN) serial bus protocol network, an ISOBUS network, etc.) includes a pump 1256 for pumping fluid from a storage tank(s) 1290 to application units 1280, 1281, . . . N of the implement, sensors 1252 (e.g., speed sensors, seed sensors for detecting passage of seed, sensors for detecting characteristics of soil or a trench including soil moisture, soil organic matter, soil temperature, seed presence, seed spacing, percentage of seeds firmed, and soil residue presence, downforce sensors, actuator valves, moisture sensors or flow sensors for a combine, speed sensors for the machine, seed force sensors for a planter, fluid application sensors for a sprayer, or vacuum, lift, lower sensors for an implement, flow sensors, etc.), controllers 1254 (e.g., GPS receiver), and the processing system 1262 for controlling and monitoring operations of the implement. The pump controls and monitors the application of the fluid to crops or soil as applied by the implement. The fluid application can be applied at any stage of crop development including within a planting trench upon planting of seeds, adjacent to a planting trench in a separate trench, or in a region that is nearby to the planting region (e.g., between rows of corn or soybeans) having seeds or crop growth.

For example, the controllers may include processors in communication with a plurality of seed sensors. The processors are configured to process data (e.g., fluid application data, seed sensor data, soil data, furrow or trench data) and transmit processed data to the processing system 1262 or 1220. The controllers and sensors may be used for monitoring motors and drives on a planter including a variable rate drive system for changing plant populations. The controllers and sensors may also provide swath control to shut off individual rows or sections of the planter. The sensors and controllers may sense changes in an electric motor that controls each row of a planter individually. These sensors and controllers may sense seed delivery speeds in a seed tube for each row of a planter.

The network interface 1260 can be a GPS transceiver, a WLAN transceiver (e.g., WiFi), an infrared transceiver, a Bluetooth transceiver, Ethernet, or other interfaces from communications with other devices and systems including the machine 1202. The network interface 1260 may be integrated with the implement network 1250 or separate from the implement network 1250 as illustrated in FIG. 9.

The processing system 1262 communicates bi-directionally with the implement network 1250, network interface 1260, and I/O ports 1266 via communication links 1241-1243, respectively.

The implement communicates with the machine via wired and possibly also wireless bi-directional communications 1204. The implement network 1250 may communicate directly with the machine network 1210 or via the network interfaces 1215 and 1260. The implement may also by physically coupled to the machine for agricultural operations (e.g., planting, harvesting, spraying, etc.).

The memory 1205 may be a machine-accessible non-transitory medium on which is stored one or more sets of instructions (e.g., software 1206) embodying any one or more of the methodologies or functions described herein. The software 1206 may also reside, completely or at least partially, within the memory 1205 and/or within the processing system 1220 during execution thereof by the system 1200, the memory and the processing system also constituting machine-accessible storage media. The software 1206 may further be transmitted or received over a network via the network interface 1215.

In one embodiment, a machine-accessible non-transitory medium (e.g., memory 1205) contains executable computer program instructions which when executed by a data processing system cause the system to performs operations or methods of the present disclosure. While the machine-accessible non-transitory medium (e.g., memory 1205) is shown in an exemplary embodiment to be a single medium, the term "machine-accessible non-transitory medium" should be taken to include a single medium or multiple media (e.g., a centralized or distributed database, and/or associated caches and servers) that store the one or more sets of instructions. The term "machine-accessible non-transitory medium" shall also be taken to include any medium that is capable of storing, encoding or carrying a set of instructions for execution by the machine and that cause the machine to perform any one or more of the methodologies of the present disclosure. The term "machine-accessible non-transitory medium" shall accordingly be taken to include, but not be limited to, solid-state memories, optical and magnetic media, and carrier wave signals.

Any of the following examples can be combined into a single embodiment or these examples can be separate embodiments. In one example of a first embodiment, a processing system comprises processing logic to execute instructions for processing agricultural data and performing speed control of a machine and associated implement during a transition period for adjusting a setting of an agricultural parameter. A communication unit is coupled to the processing logic. The communication unit to transmit and receive agricultural data from the implement. The processing logic is configured to execute instructions to generate a signal to adjust the setting of the agricultural parameter, and to determine a desired speed control during the transition period based on a desired transition distance and productivity for the transition period.

In one example of a second embodiment, a computer-implemented method for optimizing speed control during adjustment of a setting of an agricultural parameter comprises receiving agricultural data from an implement, generating a signal to adjust the setting of the agricultural parameter, and determining a desired speed control for the implement during a transition period for adjusting the setting based on a desired transition distance or productivity during the transition period.

What is claimed is:

1. A processing system comprising:
   processing logic including one or more processors is configured to execute instructions for processing agricultural data and performing speed control of a machine and associated implement during a transition period for adjusting a setting of an agricultural parameter; and
   a communication unit coupled to the processing logic, the communication unit including a transmitter and a receiver are configured to transmit and receive agricultural data from the implement, wherein the processing logic is configured to execute instructions to generate a signal to adjust the setting of the agricultural parameter from a first setpoint to a second setpoint, and to determine a desired speed control during the transition period based on a desired transition distance or productivity for the transition period, wherein adjusting a setting of the agricultural parameter from a first setpoint to a second setpoint comprises one or more of changing a population of planted seeds by a controlling a seed meter, changing seed variety, changing application rate of fertilizer, fungicide, or insecticide, changing applied downforce, or upforce to a gauge wheel that is adjacent to a furrow formed by the implement, and controlling the force applied by a row cleaner of the implement, wherein to determine a desired speed control during the transition period from the first setpoint to the second setpoint comprises determining whether one of a shortest transition distance, a productivity being optimized during the transition period by reducing speed of the machine and associated implement from a first speed to a lower second speed for productivity and then returning the machine to the first speed after the transition period ends, or a maximum transition distance during the transition period is desired, wherein the processing logic is configured to execute instructions to control the speed of the implement during the transition period based on the determined desired speed control.

2. The processing system of claim 1, wherein the processing system optimizes shortest transition distance when the setting of the agricultural parameter is adjusted by slowing the machine and associated implement to a stop as soon as possible, adjusting the setting during the transition period, and then restarting machine movement.

3. The processing system of claim 1, wherein the processing system optimizes for productivity during the transition period by reducing speed of the machine and associated implement to a minimum tolerable speed for productivity.

4. The processing system of claim 1, wherein the processing system optimizes for the maximum transition distance by reducing a speed of the machine and associated implement to a specific value that achieves a specific distance in a specific transition period.

5. The processing system of claim 1, wherein adjusting a setting of an agricultural parameter comprises one or more of changing furrow depth for planting seeds in the furrow, changing application rate of fertilizer, fungicide, or insecticide, changing applied downforce or upforce of an agricultural implement, and controlling the force applied by a row cleaner of an agricultural implement.

6. The processing system of claim 1, wherein the communication unit is configured to receive soil measurements obtained from sensors of the implement.

7. The processing system of claim 6, wherein the processing logic is configured to execute instructions to generate a signal to adjust the setting of the agricultural parameter in response to obtaining soil measurements.

8. The processing system of claim 7, wherein the soil measurements and control of implement include:
   A) moisture, organic matter, porosity, or texture/type of soil to change a population of planted seeds by controlling a seed meter;
   B) moisture, organic matter, porosity, or texture/type of soil to change seed variety;
   C) moisture, organic matter, porosity, or texture/type of soil to change furrow depth;
   D) moisture, organic matter, porosity, or texture/type of soil to change application rate offertilizer, fungicide, and/or insecticide;
   E) moisture, organic matter, porosity, or texture/type of soil to change applied downforce or upforce of an agricultural implement; or
   F) furrow residue to control the force applied by a row cleaner.

9. The processing system of claim 1, wherein the communication unit communicates with an implement network of the implement via a controller area network (CAN) serial bus protocol network or an ISOBUS network.

10. The processing system of claim 1, wherein the processing system is positioned on the machine, wherein the machine comprises a vehicle.

11. A computer-implemented method for optimizing speed control during adjustment of a setting of an agricultural parameter, the method comprising:
receiving agricultural data from an implement;
generating a signal to adjust the setting of the agricultural parameter;
determining a desired speed control for the implement during a transition period for adjusting the setting from a first setpoint to a second setpoint based on a desired transition distance or productivity during the transition period; and
controlling the speed of the implement during the transition period based on the determined desired speed control, wherein adjusting a setting of the agricultural parameter from a first setpoint to a second setpoint comprises one or more of changing a population of planted seeds by a controlling a seed meter, changing seed variety, changing application rate of fertilizer, fungicide, or insecticide, changing applied downforce, or upforce to a gauge wheel that is adjacent to a furrow formed by the implement, and controlling the force applied by a row cleaner of the implement, wherein determining a desired speed control during the transition period from the first setpoint to the second setpoint comprises determining whether one of a shortest transition distance, a productivity being optimized during the transition period by reducing speed of the machine and associated implement from a first speed to a lower second speed for productivity and then returning the machine to the first speed after the transition period ends, or a maximum transition distance during the transition period is desired.

12. The computer-implemented method of claim 11, wherein determining a desired speed control during the transition period comprises determining, with a processing system, whether a shortest transition distance, a productivity, or a maximum transition distance during the transition period is desired.

13. The computer-implemented method of claim 12, wherein the processing system optimizes shortest transition distance when the setting of the agricultural parameter is adjusted by slowing a vehicle and associated implement from a first speed to a stop as soon as possible, adjusting the setting during the transition period, and then restarting vehicle movement to the first speed.

14. The computer-implemented method of claim 12, wherein the processing system optimizes for productivity during the transition period by reducing speed of the vehicle and associated implement from a first speed to a minimum tolerable second speed for productivity during the transition period and then returns the vehicle to the first speed after the transition periods ends.

15. The computer-implemented method of claim 12, wherein the processing system optimizes for the maximum transition distance by reducing a speed of the vehicle and associated implement from a first speed to a specific second speed that achieves a specific distance in a specific transition period.

16. The computer-implemented method of claim 11, wherein adjusting a setting of an agricultural parameter comprises one or more of changing a population of planted seeds by controlling a seed meter, changing seed variety, changing furrow depth, changing application rate of fertilizer, fungicide, or insecticide, changing applied downforce or upforce of an agricultural implement, and controlling the force applied by a row cleaner of an agricultural implement.

17. The computer-implemented method of claim 11, wherein a communication unit of the vehicle is configured to receive soil measurements obtained from sensors of the implement.

18. The processing system of claim 17, wherein generating a signal to adjust the setting of the agricultural parameter occurs in response to obtaining soil measurements.

19. The computer-implemented method of claim 17, wherein the communication unit communicates with an implement network of the implement via a controller area network (CAN) serial bus protocol network or an ISOBUS network.

* * * * *